United States Patent
Mochizuki (10) Patent No.: US 6,263,093 B1
(45) Date of Patent: Jul. 17, 2001

(54) THREE-DIMENSIONAL ULTRASOUND IMAGE PROCESSING APPARATUS AND COORDINATE TRANSFORMATION METHOD USED IN THE APPARATUS

(75) Inventor: Takashi Mochizuki, Tokyo (JP)

(73) Assignee: Aloka Co., Ltd. (JP)

( * ) Notice: Subject to any disclaimer, the term of this patent is extended or adjusted under 35 U.S.C. 154(b) by 0 days.

(21) Appl. No.: 09/273,674

(22) Filed: Mar. 22, 1999

(30) Foreign Application Priority Data

Mar. 20, 1998 (JP) .................................................. 10-071774

(51) Int. Cl.$^7$ ...................................................... G06K 9/00
(52) U.S. Cl. ............................................................. 382/128
(58) Field of Search .................................... 382/128, 131, 382/130, 132; 600/407, 437; 128/915, 916; 348/163; 73/602

(56) References Cited

U.S. PATENT DOCUMENTS

| | | | |
|---|---|---|---|
| 5,010,528 | * 4/1991 | Ohtsuki et al. | 367/90 |
| 5,078,145 | * 1/1992 | Furuhata | 600/443 |
| 5,329,929 | * 7/1994 | Sato et al. | 600/441 |
| 5,396,890 | 3/1995 | Weng | 600/443 |
| 5,497,776 | * 3/1996 | Yamazaki et al. | 600/445 |
| 5,538,004 | * 7/1996 | Bamber | 600/443 |
| 5,608,849 | * 3/1997 | King, Jr. | 345/419 |
| 5,787,889 | * 8/1998 | Edwards et al. | 600/443 |
| 5,797,845 | * 8/1998 | Barabash et al. | 600/443 |
| 5,954,653 | * 9/1999 | Hatfield et al. | 600/443 |

FOREIGN PATENT DOCUMENTS

WO 91/03792 3/1991 (WO) .............................. G06F/15/42
WO 96/00402 1/1996 (WO) .............................. G01S/7/52

* cited by examiner

*Primary Examiner*—Andrew W. Johns
*Assistant Examiner*—Shervin Nakhjavan
(74) *Attorney, Agent, or Firm*—Marger Johnson & McCollom, P.C.

(57) ABSTRACT

A three-dimensional ultrasound image processing apparatus includes three-dimensional probe for forming scanning planes successively by ultrasound beam scanning to acquire three-dimensional data specified by the depth r in the ultrasound beam direction, the angle θ of the ultrasound beam with respect to a scanning start position in the respective scanning plane and the displacement angle Φ of the scanning plane; two-dimensional coordinate transformation section for transforming the depth r and the angle θ for the respective scanning plane to two-dimensional coordinates (x, y); two two-dimensional memories for sequentially storing the two-dimensional data for the respective scanning planes with each scanning plane as a unit, in which the two-dimensional data is written into an address specified by the two-dimensional coordinates (x, y) determined by the two-dimensional coordinate transformation section; three-dimensional coordinate transformation section for calculating three-dimensional coordinates (X, Y, Z) by transforming the displacement angle Φ of the scanning plane and the two-dimensional coordinates (x, y), wherein the two-dimensional coordinate x is made to correspond to the three-dimensional coordinate X; a three-dimensional memory for storing the three-dimensional data for each scanning plane, in which the two-dimensional coordinates (x, y) and the displacement angle Φ are respectively written into addresses specified by the three-dimensional coordinates (X, Y, Z) determined by the three-dimensional coordinate transformation section; and a display for producing a three-dimensional ultrasound image based on the three-dimensional data outputted from the three-dimensional memory.

31 Claims, 7 Drawing Sheets

THREE-DIMENSIONAL ULTRASOUND IMAGE PROCESSING APPARATUS AND COORDINATE TRANSFORMATION METHOD USED IN THE APPARATUS

BACKGROUND OF THE INVENTION

1. Field of the Invention

This invention relates to a three-dimensional ultrasound image processing apparatus and a coordinate transformation method used in the apparatus, and more particularly to a three-dimensional ultrasound image processing apparatus which forms a three-dimensional ultrasound image based on three-dimensional image data obtained by scanning a three-dimensional region and a coordinate transformation method used in the apparatus.

2. Description of the Prior Art

Three-dimensional image processing apparatuses include various kinds of apparatuses such as a three-dimensional ultrasound image processing apparatus and a three-dimensional X-ray image processing apparatus. A three-dimensional ultrasound image processing apparatus has the function of acquiring three-dimensional echo data and the function of processing thus acquired three-dimensional echo data (hereinafter, the "three-dimensional echo data" is also referred to simply as "three-dimensional data").

More specifically, according to the three-dimensional image processing apparatuses, a scanning plane (two-dimensional data acquiring region) is formed by electronic scanning using an array transducer having a plurality of transducer elements, and a three-dimensional data acquiring region (space) is formed by successively forming numbers of such scanning planes with displacing (pivotally swinging or rotating) the array transducer. The three-dimensional echo data obtained from this three-dimensional data acquiring region is sent to a three-dimensional image processing circuit via a signal processing circuit. Then, by reconstructing the three-dimensional echo data, a three-dimensional ultrasound image for the three-dimensional data acquiring region is formed. Such a processing is also performed in a three-dimensional X-ray image processing apparatus.

Now, in a conventional three-dimensional ultrasound image processing apparatus, each of echo data for the three-dimensional echo data acquiring region is temporarily stored in a three-dimensional echo data memory which has a storage region corresponding to the three-dimensional data acquiring region. In this case, each of the echo data is represented by the three-dimensional polar coordinates in which each data is defined by the depth r of the data on the ultrasound beam, the angle θ of the ultrasound beam relative to the scanning start position (beam) in the scanning plane and the displacement angle Φ of the scanning plane. Therefore, when the echo data is to be stored in the three-dimensional echo data memory, each of echo data is subjected to a coordinate transformation by which the three-dimensional polar coordinates are transformed into the three-dimensional orthogonal coordinates (X, Y, Z). In other words, each of echo data is stored in an address of the memory specified by the three-dimensional orthogonal coordinates, and thus stored echo data will be reconstructed to form the three-dimensional image.

However, such transformation of the three-dimensional polar coordinates into the three-dimensional orthogonal coordinates requires a large amount of arithmetic operations, and such an increased operational amount causes a problem in that it takes a long time for processing the data. In this connection, it is naturally preferable to make the time from data acquisition to image display as short as possible, and if feasible, it is desired to display the three-dimensional image in real time. In order to resolve such a problem, it may be possible to reduce the time for arithmetic operations through the use of a high speed processor or the like. In such a case, however, there arises other problem in that the cost for the image processing apparatus is markedly increased.

Moreover, in forming such a three-dimensional ultrasound image, it is necessary to carry out interpolation between ultrasound beams (lines) and interpolation between scanning planes (frames). However, execution of these interpolations for the data for the three-dimensional coordinate space also requires, a large amount of arithmetic operations as stated in the above. This also makes it difficult to shorten the time for arithmetic operations.

Further, it is to be noted that the above problems are not limited to the case of a three-dimensional ultrasound image processing apparatus, and other three-dimensional image processing apparatuses also involve such problems.

SUMMARY OF THE INVENTION

The present invention has been made in view of the problems described above. Therefore, an object of the present invention is to provide a three-dimensional image processing apparatus which can perform writing of three-dimensional data to a three-dimensional data memory in a short time and at a high speed.

Another object of the present invention is to provide a three-dimensional image processing apparatus which can produce a three-dimensional image through a reduced amount of arithmetic operations.

Other object of the present invention is to provide a three-dimensional image processing apparatus which can perform interpolation of three-dimensional data in a short time and at a high speed.

In order to achieve the above objects, the present invention is directed to a three-dimensional ultrasound image processing apparatus. The apparatus comprises:

three-dimensional data acquiring means which forms scanning planes successively by ultrasound beam scanning to acquire three-dimensional data for a three-dimensional data acquiring region, each three-dimensional data being specified by two dimensional data represented by first and second values defining each scanning plane and relative positional information of the scanning plane with respect to a predetermined scanning plane;

two-dimensional coordinate transformation means for transforming the first and second values for the respective scanning plane into two-dimensional data represented by two-dimensional coordinates (x, y);

two-dimensional data storage means for sequentially storing the two-dimensional data for the respective scanning plane with one scanning plane as a unit, in which the two dimensional data for the respective scanning plane is written into an address specified by the two-dimensional coordinates (x, y) determined by the two-dimensional coordinate transformation means;

three-dimensional coordinate transformation means for transforming the three-dimensional data defined by the two-dimensional data represented by the two-dimensional coordinates (x, y) and the relative positional information of the respective scanning plane into three-dimensional data represented by three-dimensional coordinates (X, Y, Z), in which the two-dimensional coordinate x is made to correspond to the three-dimensional coordinate X;

three-dimensional data storage means for storing the three-dimensional data for each of the scanning planes which is defined by the two-dimensional data represented by the two-dimensional coordinates (x, y) outputted from the two-dimensional data storage means and the relative positional information of each scanning plane, in which the three-dimensional data for each scanning plane is written into an address specified by the three-dimensional coordinates (X, Y, Z) determined by three-dimensional coordinate transformation means; and three-dimensional ultrasound image producing means for producing a three-dimensional ultrasound image based on the three-dimensional data outputted from the three-dimensional data storage means.

According to this three-dimensional ultrasound image processing apparatus, two-dimensional data (two-dimensional echo data) defining the respective scanning plane are temporarily written into the two-dimensional data storage means (intermediate storage) with each scanning plane as a unit, rather than being written directly into the three-dimensional data storage means. In this case, the address (x, y) to be written is generated by performing coordinate transformation in the two-dimensional coordinate transformation means. The amount of the arithmetic operations required for the coordinate transformation between two-dimensional coordinate systems such as a coordinate transformation from the two-dimensional polar coordinates to the two-dimensional orthogonal coordinates is very small in comparison with that required for the coordinate transformation from the three-dimensional polar coordinates to the three-dimensional orthogonal coordinates. Moreover, the coordinate transformation from the two-dimensional polar coordinates to the two-dimensional orthogonal coordinates can be accomplished utilizing the functions of an existing scanning converter (for example, digital scan converter (DSC)).

Next, the three-dimensional data read out from the two-dimensional data storage means are written into the three-dimensional data storage means. In this case, the address (X, Y, Z) to be written is generated by performing coordinate transformation in the three-dimensional coordinate transformation means. In this coordinate transformation, the three-dimensional coordinates (X, Y, Z) are specified based on the two-dimensional coordinates (x, y) and the relative positional information of the scanning plane such as the displacement angle Φ of the scanning plane. However, since the two-dimensional coordinate x corresponds to the three-dimensional coordinate X (a linear transformation may be involved as needed), it can be understood that this coordinate transformation is in substance accomplished by a transformation from two-dimensional coordinate system to another two-dimensional coordinate system. The amount of the arithmetic operations performed for this coordinate transformation is very small in comparison with that in the conventional three-dimensional coordinate transformation by the same reason as mentioned in the above. Consequently, according to this invention, the total amount of the arithmetic operations required for the transformation from the three-dimensional polar coordinates to the three-dimensional orthogonal coordinates can be drastically reduced in comparison with that required in the conventional case.

Furthermore, the present invention may be applied to the case where the three-dimensional image formation function is additionally provided in an existing image processing apparatus for forming two-dimensional images. Namely, since the two-dimensional coordinate transformation is also carried out in an existing two-dimensional ultrasound diagnostic apparatus or the like, the existing apparatus is equipped with a device for carrying out the two dimensional coordinate transformation such as a two-dimensional digital scan converter (DSC). Therefore, when the present invention is applied to the two-dimensional image processing apparatus to add the three-dimensional image formation function thereto, there is an advantage that it is possible to share the components for carrying out the coordinate transformation by using the device for performing the two dimensional coordinate transformation. Such sharing of the existing device will make it possible to reduce the manufacturing cost.

In the three-dimensional ultrasound image processing apparatus of the present invention, it is preferred that each of the two-dimensional data defining the respective scanning plane is written into the two-dimensional storage means so that the center axis of the respective scanning plane is in parallel with the y axis of the two-dimensional coordinate system. Further, it is also preferred that the three-dimensional data acquiring means includes an array transducer, means for causing the array transducer to perform electronic beam scanning and means for displacing the array transducer pivotally with respect to a virtual rotational axis which is in parallel with a line connecting the both ends of the array transducer so as to form numbers of scanning planes.

Furthermore, in the three-dimensional ultrasound image processing apparatus of the present invention, it is also preferred that the three-dimensional coordinate transformation means utilizes the x value of the two-dimensional coordinates as it is for the X value of the three-dimensional coordinates.

Moreover, it is also preferred that the two dimensional data represented by first and second values defining each scanning plane is represented by polar coordinates (r, θ). In this case, it is preferred that the first value represents the depth r in the ultrasound beam direction, and the second value represents the angle θ of the ultrasound beam with respect to a predetermined ultrasound beam in the respective scanning plane.

Preferably, the relative positional information of the respective scanning plane is an angle Φ of the respective scanning plane with respect to a predetermined scanning plane. In this case, it is preferred that the predetermined scanning plane is a scanning plane initially formed.

Further, it is also preferred that the predetermined ultrasound beam in the respective scanning plane is an ultrasound beam at a scanning start position in the respective scanning plane.

Furthermore, it is also preferred that the respective scanning plane has a center axis, and each of the three-dimensional data is written into the two-dimensional storage means so that the center axis of the respective scanning plane is in parallel with the y axis of the two-dimensional coordinates (x, y). In this case, it is preferred that the three-dimensional data acquiring means includes an array transducer having both ends, means for causing the array transducer to perform electronic beam scanning and means for pivotally displacing the array transducer for forming the successive scanning planes with respect to a virtual rotational axis which is in parallel with a line connecting the both ends of the array transducer. In this case, the displacement of the array transducer maybe carried out manually or by an array transducer displacement device.

Furthermore, it is preferred that the respective scanning plane has a center axis, and each of the three-dimensional data is written into the two-dimensional storage means so that the center axis of the respective scanning plane is in parallel with the x axis of the two-dimensional coordinates (x, y). In this case, preferably, the three-dimensional data acquiring means includes an array transducer, means for causing the array transducer to perform electronic beam scanning and means for rotating the array transducer with respect to the central axis for obtaining the successive scanning planes.

Moreover, it is also preferred that the relative positional information of the respective scanning plane is an amount of displacement of the respective scanning plane with respect to a predetermined scanning plane. In this case, preferably, the three-dimensional data acquiring means includes an array transducer, means for causing the array transducer to perform electronic beam scanning and means for displacing the array transducer for forming the successive scanning planes. Further, the displacement of the scanning plane may be carried out manually or by an array transducer displacement device.

Further, in the present invention, the two dimensional data represented by first and second values defining each scanning plane may be represented by orthogonal coordinates (x', y') which are different from the two-dimensional coordinates (x, y). In this case, the first value represents the position of each of the ultrasound beams and the second value represents the depth of the sampling point in each ultrasound beam in the ultrasound beam direction. Further, it is preferred that the three-dimensional data acquiring means includes an array transducer, means for causing the array transducer to perform electronic beam scanning and means for displacing the array transducer for forming the successive scanning planes. The displacement of the scanning plane can be carried out manually or by an array transducer displacement device.

Furthermore, it is preferred that the three-dimensional ultrasound image processing apparatus further comprises interpolation means for producing interpolation data that interpolates between adjacent ultrasound beams in the respective scanning plane. Moreover, it is also preferred that three-dimensional ultrasound image processing apparatus further comprises scanning plane interpolation means for producing interpolation data that interpolates between adjacent scanning planes. In performing an interpolation calculation by the beam interpolation means or the scanning plane interpolation means described above, the interpolation processing is performed substantially for the data on the two-dimensional coordinate. Therefore, the interpolation processing for the three-dimensional data can be performed in a short time and at a high speed.

Another aspect of the present invention is directed to a three-dimensional ultrasound image processing apparatus. The apparatus comprises:

three-dimensional data acquiring means which forms scanning planes successively by ultrasound beam scanning to acquire three-dimensional data for a three-dimensional data acquiring region, each three-dimensional data being specified by two dimensional data defining each scanning plane and relative positional information of the scanning plane with respect to a predetermined scanning plane;

beam interpolation means for producing interpolation data that interpolates between adjacent ultrasound beams in each of the respective scanning planes, whereby forming interpolated two-dimensional data for each scanning plane;

a pair of two-dimensional data storage means for sequentially storing the interpolated two-dimensional data for the respective scanning plane with one scanning plane as a unit, respectively;

frame interpolation means for producing interpolation data that interpolates between the adjacent scanning planes using the data for the adjacent two scanning planes which are outputted from the pair of the two-dimensional data storage means and which have been undergone the beam interpolation, respectively; and three-dimensional data storage means for storing three-dimensional data comprised of the data for the interpolated scanning planes and the relative positional information of the respective scanning; and three-dimensional ultrasound image producing means for producing a three-dimensional ultrasound image based on the three-dimensional data outputted from the three-dimensional data storage means.

The other aspect of the present invention is directed to a coordinate transformation method used in a three-dimensional ultrasound image processing apparatus. The method comprises the steps of: forming numbers of scanning planes successively by ultrasound beam scanning to acquire three-dimensional data from a three-dimensional data acquiring region, each three-dimensional data being specified by two dimensional data represented by first and second values defining each scanning plane and relative positional information of the scanning plane with respect to a predetermined scanning plane;

transforming the first and second values for the respective scanning plane into two-dimensional data represented by two-dimensional coordinates (x, y);

sequentially storing the two-dimensional data for the respective scanning plane with one scanning plane as a unit, in which the two dimensional data for the respective scanning plane is written into an address specified by the two-dimensional coordinates (x, y) determined by the two-dimensional coordinate transformation means;

transforming the three-dimensional data defined by the two-dimensional data represented by the two-dimensional coordinates (x, y) and the relative positional information of the respective scanning plane into three-dimensional data represented by three-dimensional coordinates (X, Y, Z), in which the two-dimensional coordinate x is made to correspond to the three-dimensional coordinate X;

storing the three-dimensional data for each of the scanning planes which is defined by the two-dimensional data represented by the two-dimensional coordinates (x, y) outputted from the two-dimensional data storage means and the relative positional information of each scanning plane, in which the three-dimensional data for each scanning plane is written into an address specified by the three-dimensional coordinates (X, Y, Z) determined by three-dimensional coordinate transformation means; and producing a three-dimensional ultrasound image based on the three-dimensional data outputted from the three-dimensional data storage means.

Other objects, configurations and advantages of this invention will be apparent from the following description of the embodiments which is described in conjunction with the accompanying drawings.

DETAILED DESCRIPTION OF THE PREFERRED EMBODIMENTS

Hereinbelow, preferred embodiments of the present invention will be described with reference to the accompanying drawings.

Figure 1:
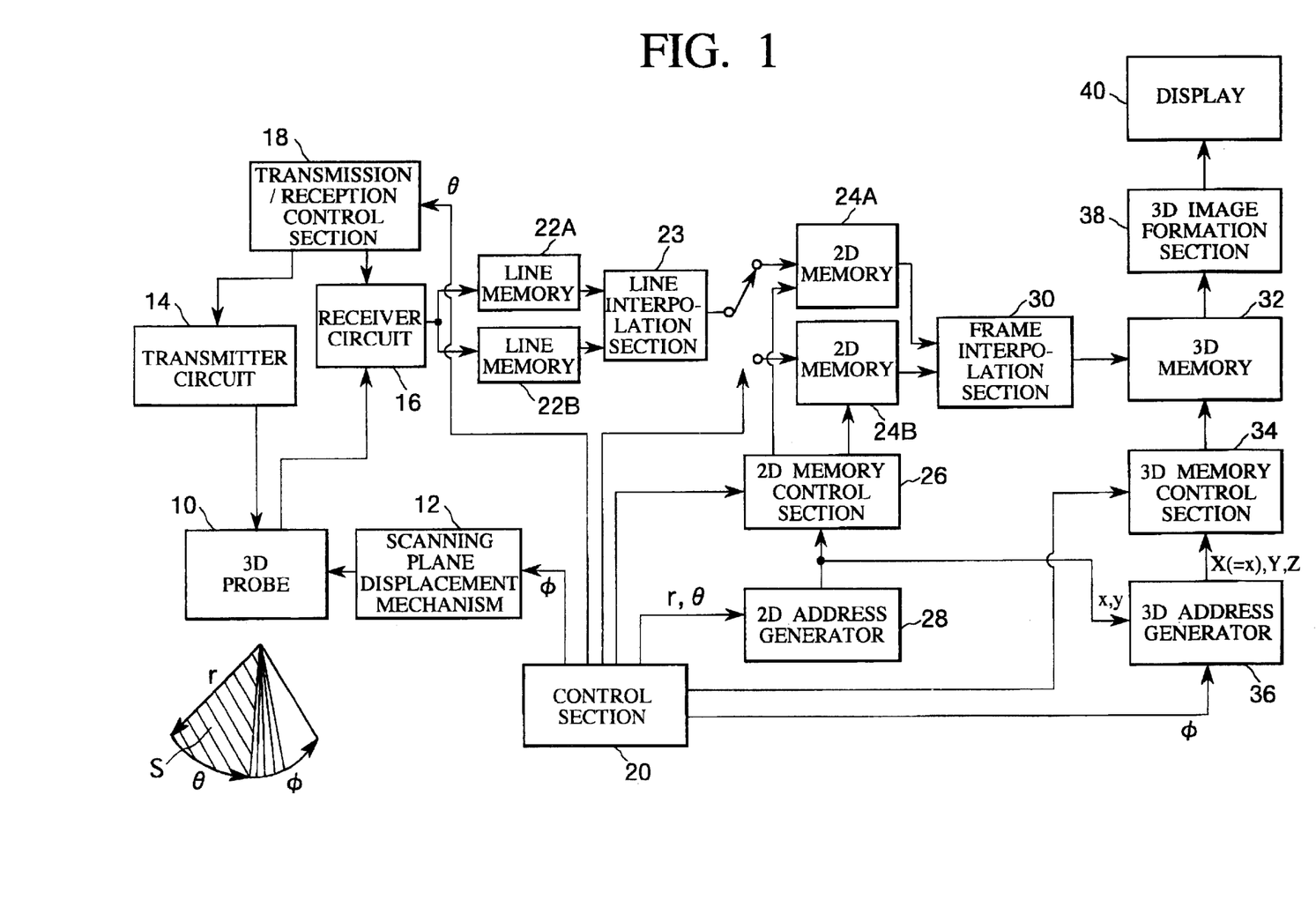
FIG. 1 is a block diagram which shows an embodiment of the three-dimensional ultrasound image processing apparatus according to the present invention.

FIG. 1 is a block diagram which shows an overall structure of an embodiment of a three-dimensional ultrasound image processing apparatus according to the present invention. In this embodiment, the three-dimensional ultrasound image processing apparatus is an ultrasound diagnostic apparatus provided with a three-dimensional ultrasound image formation function.

In FIG. 1, the reference numeral 10 denotes a three-dimensional probe which is an ultrasound probe for acquiring three-dimensional data. By this ultrasound probe 10, ultrasound beams are transmitted and echoes thereof are received to form a scanning plane. Namely, the scanning plane is formed by performing electronic beam scanning with the ultrasound beams. Further, a three-dimensional echo data acquiring region is formed by displacing the ultrasound probe 10, namely by pivotally swinging the ultrasound probe 10 as shown in FIG. 2A or by rotating the ultrasound probe 10 as shown in FIG. 2B, to form numbers of scanning planes successively.

Figure 2A:
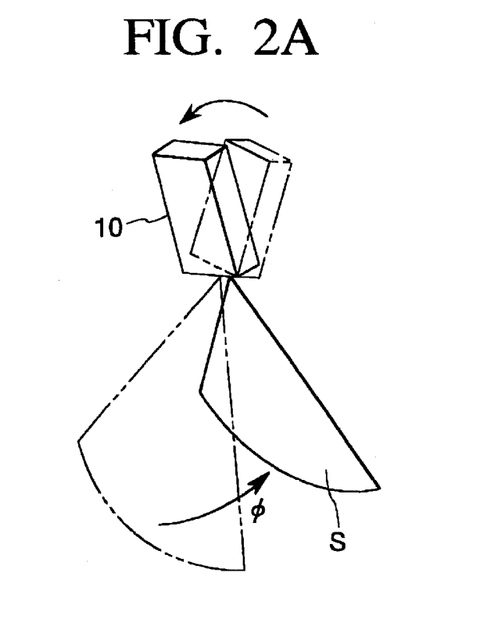
FIGS. 2A, 2B, 2C and 2D are diagrams which illustrate the scanning methods by a three-dimensional probe, respectively.
Figure 2B:
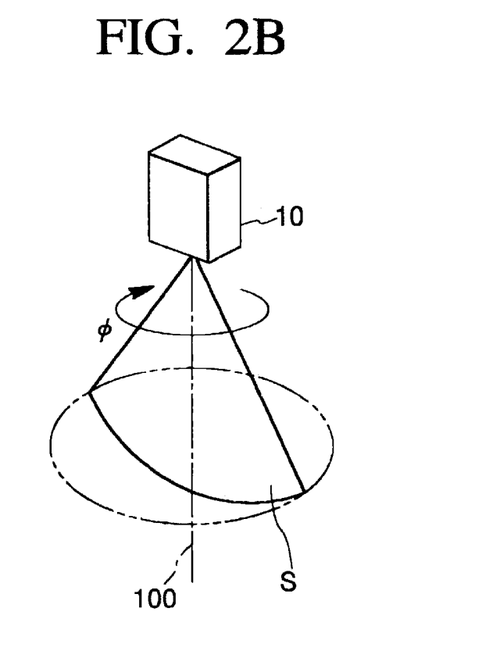

In the scanning methods shown in FIG. 2A and FIG. 2B, a sector-shaped scanning plane S is formed, in which the depth of the ultrasound in the beam direction is represented by r and the angle of the ultrasound beam with respect to the scanning start position in the scanning plane S is represented by the angle θ. In other words, the scanning plane S is defined by the values of r and θ. Namely, the scanning plane S is represented by a polar coordinate system. Further, the relative positional information of the scanning plane with respect to a predetermined scanning plane S, that is the displacement angle (angle of pivotal swing or angle of rotation) of the scanning plane S is represented by Φ.

In this embodiment, the three-dimensional probe 10 has an array transducer which is constructed from a plurality of transducer elements. The array transducer is operated electronically to perform scanning with ultrasound beams. In this regard, it is to be noted that in the present invention other scanning methods may be employed in addition to the sector scan described above. Examples of the other scanning methods include a convex scan using an array transducer arranged in a convex form (shown in FIG. 2C) and a linear scan using a linear array transducer (shown in FIG. 2D).

Further, as stated in the above, the three-dimensional probe 10 is constructed such that the scanning planes formed by the array transducer can be displaced, that is numbers of scanning planes are formed successively, to scan the three-dimensional data acquiring region. In this embodiment, the displacement of the scanning plane S is carried out by mechanically displacing the array transducer (that is, pivotally swinging or rotating the array transducer), and such displacement of the array transducer is carried out by a scanning plane displacing mechanism 12 provided with a displacement angle detection means. One example of such scanning plane displacing mechanism 12 is shown in U.S. Pat. No. 5,460,179.

There are known various ways for displacing the array transducer to form numbers of scanning planes successively. For example, as shown in FIG. 2A, it is possible to pivotally swing the array transducer of the three-dimensional probe 10 with respect to a virtual axis which is set so as to be parallel to the line that connects the both ends of the array transducer. Further, as shown in FIG. 2B, it is also possible to rotate the transducer array of the three-dimensional probe 10 with respect to the center axis 100 of the scanning plane S which vertically passes the apex of the scanning plane S. In either case, as a result of the displacement of the array transducer, a three-dimensional echo data acquiring region can be formed.

Figure 2C:
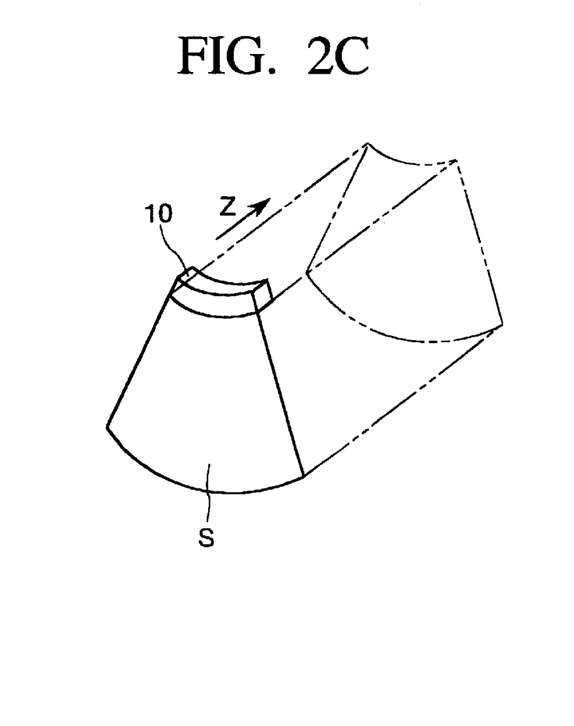
Figure 2D:
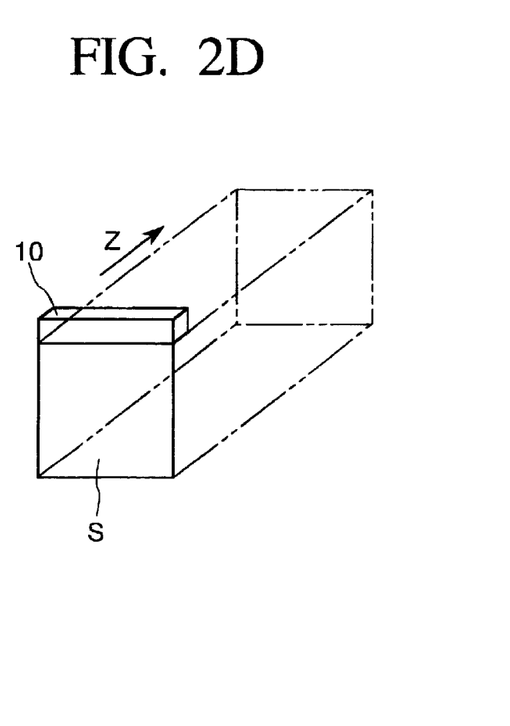

In this connection, it is to be noted that in the present invention it is also possible to displace or move the ultrasound probe 10 in the direction substantially orthogonal to the scanning plane as shown in FIG. 2C and FIG. 2D to form numbers of scanning planes successively, as described later in details. In these cases, the relative positional information of the scanning plane with respect to a predetermined scanning plane S is determined based on an amount of the displacement of the scanning plane with respect to a predetermined scanning plane S (that is, distance from a predetermined scanning plane S) represented by z. The displacement of the ultrasound probe 10 may be done using an appropriate displacing mechanism as described above.

In this embodiment, the displacement of the scanning plane S is performed mechanically as described above. However, in the present invention, the displacement of the scanning plane S (formation of numbers of the scanning planes) may be done utilizing a specific array transducer driven by electronic control, such as a two-dimensional array transducer.

Further, in the present invention, the three-dimensional probe 10 (array transducer) may be pivotally swung (or rotated) or displaced (or moved) manually. In this case, it is necessary to detect the displacement angle (pivotally swung angle or rotational angle) of the array transducer using a separate position detection sensor or attitude detection sensor.

The three-dimensional probe 10 is connected to a transmitter circuit 14 and a receiver circuit 16 which are controlled by a transmission and reception control section 18. Under the control of the transmission and reception control section 18, a transmission signal is supplied to the three-dimensional probe 10 from the transmitter circuit 14. Based on this transmission signal, an ultrasound beam is emitted into the three-dimensional region by the three-dimensional probe 10. When an ultrasound echo from the three-dimensional region is received by the three-dimensional probe 10, the received signal is inputted into the receiver circuit 16 through the three-dimensional probe 10. Then, the received signal is amplified and phase-detected by an amplifier and a phase detection circuit (not shown in the drawings).

In the transmitter circuit 14, a predetermined delay control is performed on the transmission signals to be supplied to each transducer element of the three-dimensional probe 10, in order to form transmission beams as well as carry out transmission focusing. Further, in the receiver circuit 16, a predetermined delay control is performed on the reception signals to be outputted from each transducer element of the three-dimensional probe 10, in order to obtain echo signals as well as carry out reception focusing.

The transmission and reception control section 18 is controlled by a control section 20 which supplies various kinds of parameters to the transmission/reception control section 18. Included among these parameters is information about the angle θ of the ultrasound beam with respect to the scanning start position in the scanning plane S.

The scanning plane displacement mechanism 12 is also controlled by the control section 20. Namely, the control section 20 supplies information about the relative positional information of the scanning plane S such as the displacement angle (pivotally swung angle or rotational angle) Φ of the scanning plane S to the scanning plane displacement mechanism 12. In this connection, it is to be noted that information about the depth r for each echo data is included in the reception signal outputted from the three-dimensional probe 10. The information about the depth r of the echo data is determined by the time elapsed from the transmission to the reception of the ultrasound beam.

In this embodiment, the reception signal (echo data) for the respective ultrasound beam outputted from the receiver circuit 16 is successively stored in each of two line memories 22A, 22B in the form of two-dimensional data for each ultrasound beam. The echo data in the form of two-dimensional data read out from the line memories 22A, 22B are then inputted into a line (beam) interpolation section 23 in accordance with the time sequence order for interpolation between the adjacent ultrasound beams.

The line interpolation section 23 produces virtual one or a plurality of three-dimensional interpolation data (interpolation beams) which interpolate between the adjacent two ultrasound beams within the scanning plane S.

By performing this line interpolation processing, the number of the ultrasound beams can be apparently increased, so that it is possible to improve the resolution of the three-dimensional image as described later.

In this connection, it is to be noted that in the present invention it is not always necessary to have two line memories. In the case where only one line memory is provided, as soon as two-dimensional data for one ultrasound beam has been read out from the line memory, two-dimensional data for the next ultrasound beam is written in the line memory, and then the line interpolation processing is carried out using the two-dimensional data for the two ultrasound beams.

The interpolated two-dimensional data produced in the line interpolation section 22 is successively stored in one of two-dimensional memories 24A, 24B to produce interpolated two-dimensional data for the scanning plane S. Further, in the other two-dimensional memory, two-dimensional data for the next scanning plane S based on the interpolated two-dimensional data produced in the line interpolation section 22 is then stored. The switching between the two-dimensional memories 24A, 24B is carried out by means of a switch which is controlled by the control section 20. These two-dimensional memories are formed into a so-called frame memory which can store echo data for one scanning plane, respectively.

The writing and reading out of the two-dimensional data in and from the two-dimensional memories 24A, 24B are controlled by a two-dimensional memory control section 26. In more details, the two-dimensional memory control section 26 carries out controls for writing the two-dimensional data for each scanning plane which is represented by the r and θ to a predetermined address of the two-dimensional memory represented by two-dimensional coordinates (x, y). The two dimensional memory address (x, y) is generated in a two-dimensional address generator 28. Preferably, the two dimensional memory addresses determined by the x, y coordinates correspond to the pixel arrangements in the respective two-dimensional memory (frame memory).

In more details, the two-dimensional memory control section 26 is also controlled by the control section 20. The control section 20 also provides information concerning the depth r of the ultrasound beam in the beam direction and the angle θ of the ultrasound beam with respect to the scanning start position in the scanning plane to the two-dimensional address generator 28. Based on the information concerning the r and θ, the two-dimensional address generator (two-dimensional coordinate transformation means) 28 generates an address (x, y) represented by the two-dimensional coordinates which corresponds to the r and θ. In other words, the two-dimensional address generator 28 calculates the two-dimensional coordinate values (x, y) corresponding to the r and θ by coordinate-transforming the depth r and the angle θ for each scanning plane. The control for writing the two-dimensional data to the two-dimensional memories 24A, 24B will be described in detail later.

In this regard, it is also to be noted that in the embodiment described above the two-dimensional data is written in the two-dimensional memory after being subject to the line interpolation processing. However, in the present invention, it is also possible to carry out the line interpolation when the two-dimensional data is to be read out from the two-dimensional memory.

In the following stage of the two-dimensional memories 24A, 24B, there is provided a frame interpolation section 30 for interpolation between the adjacent frames. The frame interpolation section 30 includes a circuit which generates interpolation data for one or a plurality of virtual scanning planes which are interpolated between two adjacent scanning planes. In this embodiment, in order to perform such a frame interpolation calculation, the two two-dimensional memories 24A, 24B described above are provided. In this connection, when such a frame interpolation is not performed, it is not necessarily required to have two two-dimensional memories 24A, 24B, and provision of only one memory will be sufficient.

Here, the two-dimensional data after the frame interpolation may be stored again in the two-dimensional memories. Namely, in this embodiment, the line interpolation and the frame interpolation need only be executed prior to the storage to a three-dimensional memory 32 in the form of the three-dimensional data, so the configuration shown in FIG. 1 should be understood to be only one of such examples.

Figure 3:
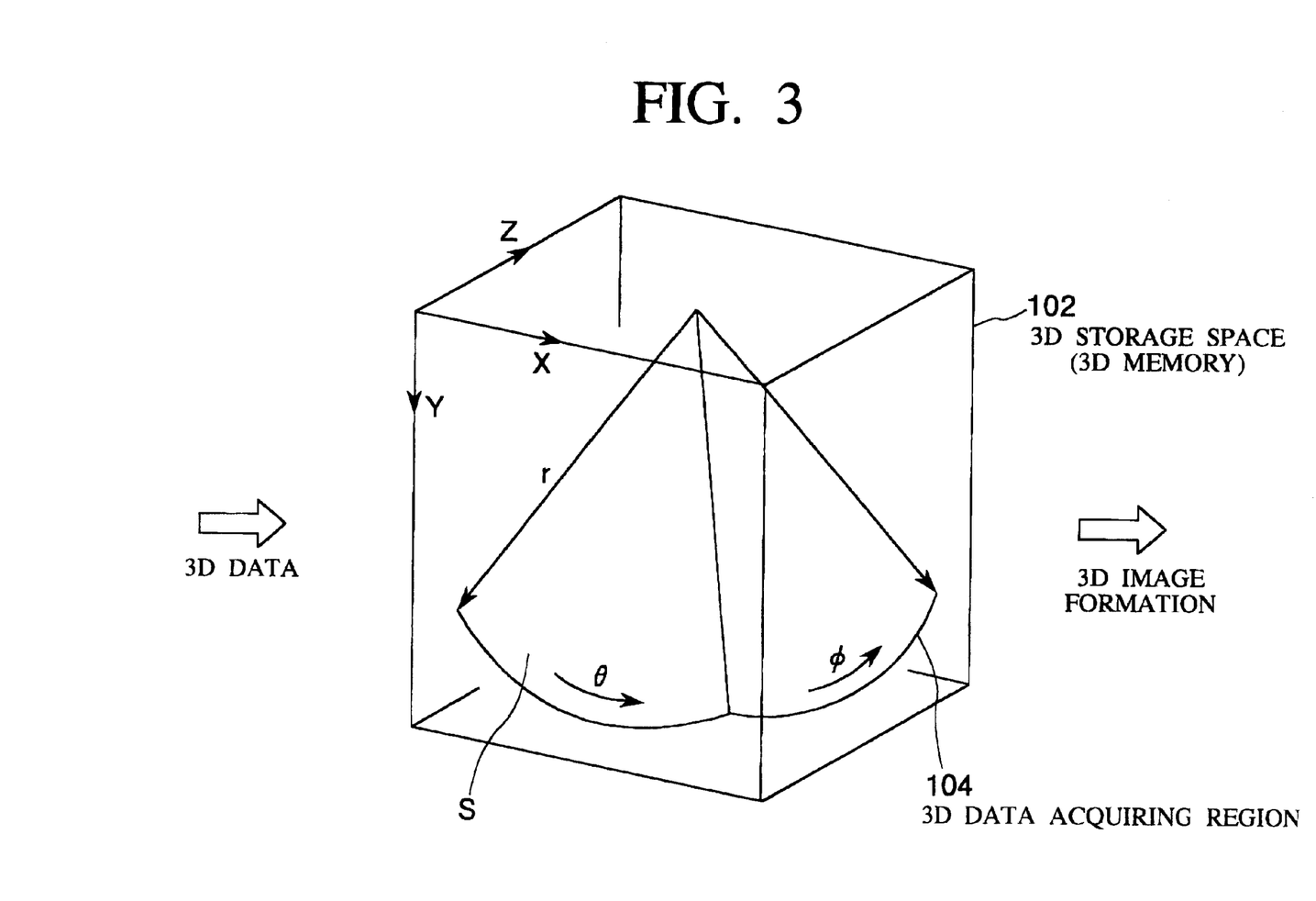
FIG. 3 is a conceptional view which shows the relationship between the storage region (space) of a three-dimensional memory and the three-dimensional data acquiring region.

In the three-dimensional memory 32, there are stored all of the three-dimensional data in the three-dimensional echo data acquiring region. The concept of this storage is illustrated in FIG. 3. In FIG. 3, a three-dimensional storage region (space) 102 corresponds to the storage region of the three-dimensional memory 32. In the storage region of the three-dimensional memory 32 corresponding to the three-dimensional storage space 102, there are stored numerous three-dimensional data constituting a three-dimensional data acquiring region 104.

In this connection, it is to be noted that in the conventional method each three-dimensional echo data is also stored in the storage region of the three-dimensional memory. This embodiment is different from the conventional method in that the data for the respective scanning plane in the form of two-dimensional data has been stored in the two-dimensional memory 24 prior to the storage to the three-dimensional memory 32 as described above.

A three-dimensional memory control section 34 shown in FIG. 1 is a means for controlling writing and reading out of three-dimensional data in and from the three-dimensional memory 32. A three-dimensional address generator (three-dimensional coordinate transformation means) 36 generates a three-dimensional address specified by orthogonal coordinates (X, Y, Z). Each of three-dimensional data is written into a memory address specified by the three-dimensional address (X, Y, Z).

In more details, the three-dimensional memory control section 34 is controlled by the control section 20. The control section 20 provides the relative positional information such as the displacement angle $\Phi$ (pivotally swung angle or rotational angle) of the scanning plane (or the amount of the displacement z) to a three-dimensional address generator 36. The three-dimensional address generator 36 is also supplied with the two-dimensional address (x, y) generated in the two-dimensional address generator 28. The three-dimensional address generator 36 derives the three-dimensional address (X, Y, Z) as described above based on the information (values) concerning x, y and $\Phi$.

In other words, the three-dimensional address generator 36 calculates the three-dimensional coordinates (X, Y, Z) by transforming the relative positional information (displacement angle $\Phi$, etc.) of the scanning plane S and the two-dimensional data for the respective scanning plane S represented by the two-dimensional coordinates (x, y). In this embodiment, however, the three-dimensional coordinate X corresponds to the two-dimensional coordinate x. Accordingly, no coordinate transformation is carried out substantially between the coordinate values x and X. As a result of such a corresponding relationship between the three-dimensional coordinates and the two-dimensional coordinates, along with the two-dimensional coordinate transformation carried out when the two-dimensional data has been stored in the two-dimensional memories 24A, 24B, it is possible to substantially reduce the amount of arithmetic operations required for the transformation of the three-dimensional coordinates, as will be described later.

In the embodiment as shown in FIG. 1, information about the two-dimensional coordinate x is supplied to the three-dimensional address generator 36 from the two-dimensional address generator 28. Instead of this, the information about x may be supplied to the three-dimensional address generator 36 as a header added to each two-dimensional data.

A three-dimensional image formation section 38 is a means for reconstructing a three-dimensional ultrasound image based on the three-dimensional data stored in the three-dimensional memory 32. In reconstruction of the three-dimensional ultrasound image, various kinds of known techniques may be applied. Then, a three-dimensional image thus obtained is displayed on a display 40.

Figure 4:
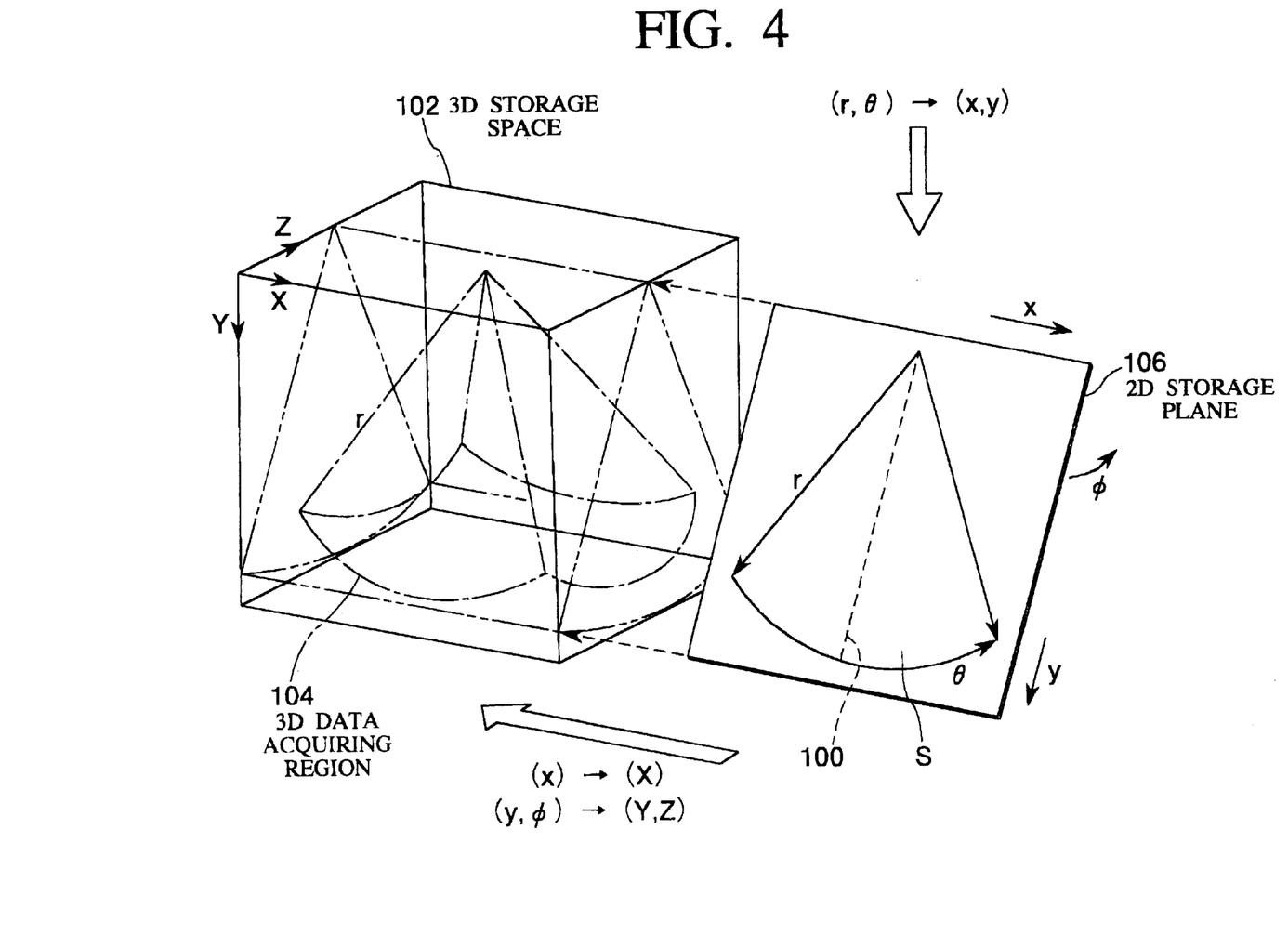
FIG. 4 is a conceptional view which shows the concept of coordinate transformation carried out in the three-dimensional memory in the case of the scanning method shown in FIG. 2A.
Figure 5:
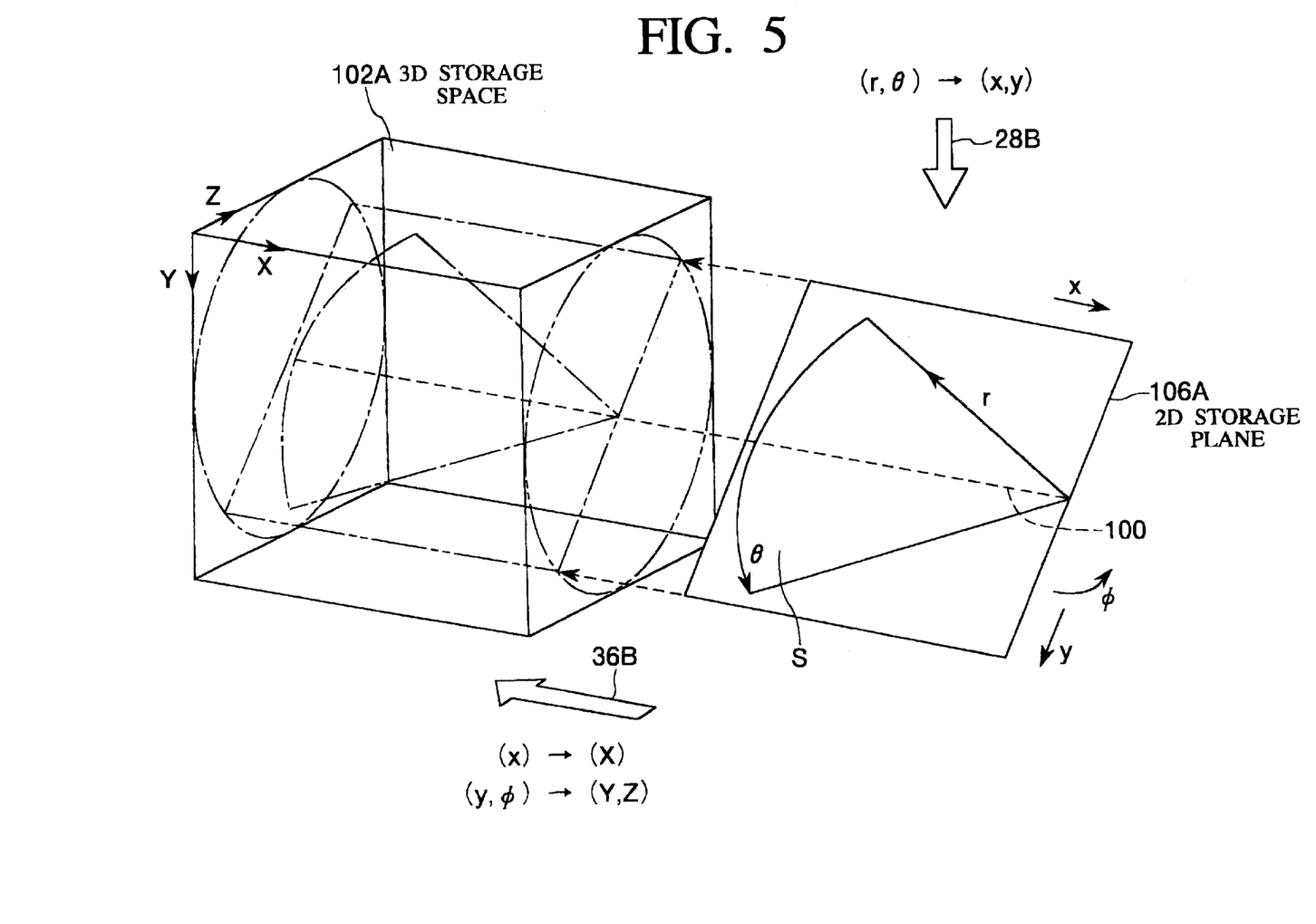
FIG. 5 is a conceptional view which shows the concept of coordinate transformation carried out in the three-dimensional memory in the case of the scanning method shown in FIG. 2B.

Next, referring to FIG. 4 and FIG. 5, the concept of the coordinate transformation carried out upon storage to the three-dimensional memory 32 according to this invention will be described, in which FIG. 4 shows a concept of the coordinate transformation carried out when the scanning shown in FIG. 2A is performed, and FIG. 5 shows a concept of the coordinate transformation carried out when the scanning shown in FIG. 2B is performed, respectively.

In FIG. 4, the three-dimensional storage space 102 corresponds to the storage region in the three-dimensional memory 32 as mentioned above. Each three-dimensional data in the three-dimensional data acquiring region 104 is eventually stored in the storage region of the three-dimensional memory 32. Prior to the storage of each three-dimensional data in the storage region of the three-dimensional memory 32, the data defining each scanning plane is stored in the two-dimensional memory 24A or 24B in the form of two-dimensional data represented by the two-dimensional coordinates (x, y) as mentioned above. The storage region of the two-dimensional memory 24A or 24B is indicated as a two-dimensional storage plane 106 in FIG. 4.

In more details, the two-dimensional data for each scanning plane S which has been specified by the depth r and the angle $\theta$ as shown in two-dimensional storage plane 106 in FIG. 4 is undergone the coordinate transformation into the two-dimensional coordinates (x, y) when the two-dimensional data for the scanning plane is stored in the two-dimensional memory as described above. Namely, the coordinate transformation from the two-dimensional polar coordinate system to the two-dimensional orthogonal coordinate system is carried out. In this embodiment, the coordinate transformation is carried out such that the center axis 100 of the sector shaped scanning plane S is in parallel with the y axis of the orthogonal coordinate system (x, y) in the two-dimensional storage plane 106.

Further, as shown in FIG. 4, each two-dimensional storage plane 106 containing the two dimensional data for the scanning plane S is accompanied with the relative positional information such as the displacement angle $\Phi$ to form three-dimensional data specifying each scanning plane within the three-dimensional space.

When the three-dimensional data for the scanning planes S are to be stored in the storage region of the three-dimensional memory 32, each of the two-dimensional data stored in the two-dimensional memory is readout by raster scan, and then stored together with the accompanied relative positional information to the corresponding address in the three-dimensional memory 32 specified by the orthogonal three-dimensional coordinates (X, Y, Z). The address (X, Y, Z) is generated in the three-dimensional address generator 36 based on the two-dimensional coordinates (x, y) and the relative positional information such as the displacement angle $\Phi$ of the scanning plane.

In this case, it is to be noted that, as described above, X in the three-dimensional space 102 coincides with x in the two-dimensional storage plane 106. Because of such a corresponding relationship, in generating the three-dimensional coordinates, only the calculation processing for obtaining the three-dimensional coordinate values Y and Z from the two-dimensional coordinate value y and the displacement angle $\Phi$ is carried out. Namely, in this coordinate transformation, it can be understood that a two-dimensional coordinate transformation from one two-dimensional coordinate system to another system is in substance carried out, and hence there is no need for carrying out a three-dimensional coordinate transformation as is done in the conventional method.

As described above, the two-dimensional echo data for the respective scanning plane is written in the storage region of the two-dimensional memory with the scanning plane as a unit. Moreover, the two-dimensional data for the respective scanning plane which is read out from the two-dimensional memory is stored in the three-dimensional memory 32 which is determined by the three-dimensional orthogonal coordinates (X, Y, Z) together with the relative positional information supplied from the three-dimensional address generator 36.

Specifically, when the two-dimensional data is read out from the two-dimensional memory, the raster scan is carried out as described above to sequentially read out the two-dimensional data in the horizontal direction (x axis direction) along the vertical direction (y axis direction). By carrying out the raster scan for each scanning plane, it is possible to write the two-dimensional data and the accompanied relative positional information for all of the scanning planes into the corresponding addresses (X, Y, Z) determined by three-dimensional address generator 36. With this result, the three-dimensional data constituting the three-dimensional data acquiring region can be stored in the three-dimensional memory 32.

Accordingly, although in this embodiment the three-dimensional data for the three-dimensional data acquiring region are also stored in the three-dimensional memory 32 of FIG. 1 in the same way as in the conventional method, a coordinate transformation between two-dimensional coordinate systems (between two-dimensional polar coordinate system and the two-dimensional orthogonal coordinate system) is carried out utilizing the two-dimensional memory 24 prior to the storage of the three-dimensional data. Because of this, according to this embodiment, it becomes possible to reduce the amount of arithmetic operations required for the transformation drastically in comparison with the conventional case in which transformation from the three-dimensional polar coordinates to the three-dimensional orthogonal coordinates is carried out at a time.

Moreover, if the line interpolation or frame interpolation is executed following the storage of the three-dimensional data in the three-dimensional memory as is doe in the conventional method, the amount of arithmetic operations required is enormous. In contrast to this, according to this embodiment, the line interpolation is executed in the next stage of the line memories 22A, 22B, the frame interpolation is executed after storage of the three-dimensional data in the two-dimensional memories 24A, 24B, and the storage of the three-dimensional data to the three-dimensional memory 32 is performed after the frame interpolation, so that there is an advantage in that the amount of arithmetic operations required for the interpolations can also be drastically reduced. In this connection, it is to be noted that the transformation from the values y and Φ to the values Y and Z shown in FIG. 4 can be realized by using y cosΦ and y sinΦ.

In a conventional ultrasound diagnostic apparatus which displays a two-dimensional tomographic image or the like, a two-dimensional memory is also employed as a frame memory. In that case, the transformation from the depth r and the angle θ to x and y, namely, the transformation from the two-dimensional polar coordinate system to the two-dimensional orthogonal coordinate system is actually performed. Therefore, the apparatus according to this embodiment can readily be realized by utilizing such an existing scanning transformation means as it is, and by adding a configuration such as the three-dimensional memory 32 in its following stage. Accordingly, there is an advantage in that the cost for manufacturing the apparatus can be reduced since the existing device and components are effectively utilized.

FIG. 5 also illustrates the concept of the coordinates transformation in the case where the scanning method shown in FIG. 2B is employed. Although this system adopts the same basic principle as that of the system shown in FIG. 4, in the storage method shown in FIG. 5, each two-dimensional data defining the scanning plane S is written so that the center axis 100 of the scanning plane S is in parallel to the x direction in a two-dimensional storage plane 106A. The coordinate x in the storage region corresponding to the two-dimensional storage plane 106A coincides with the coordinate X in a three-dimensional storage space 102A, and therefore a coordinate transformation between them is unnecessary. This is similar to the case of the embodiment shown in FIG. 4.

In the storage region of the two-dimensional memory corresponding to the two-dimensional storage plane 106A, two-dimensional data for the respective scanning planes S are stored with each scanning plane as a unit. When the two-dimensional data is to be stored, the two-dimensional coordinates x and y are determined by the coordinate transformation from the depth r and the angle θ. Namely, each two-dimensional data is written in the address specified by the two-dimensional coordinates (x, y) as is the same with the case described above.

When the two-dimensional data for one scanning plane S which is stored in the two-dimensional memory is to be read out, the raster scan is carried out in the horizontal direction (x axis direction) along the vertical direction (y axis direction) as mentioned above, and the read out two-dimensional data for the respective scanning planes and the accompanied relative positional information are written into addresses (X, Y, Z) of the three-dimensional memory 32 determined by the three-dimensional address generator 36. In this process, similar to the embodiment shown in FIG. 4, the calculation for obtaining the three-dimensional coordinate values Y and Z from the two-dimensional coordinate value y and the rotational angle Φ of the scanning plane S is carried out as a coordinate transformation. In this regard, it is to be noted that the two-dimensional coordinate x corresponds to the three-dimensional coordinate X as mentioned above.

As described in the above, even in the case of the embodiment shown in FIG. 5, it is possible write all of the three-dimensional data to the storage region of the three-dimensional memory 32 through two times of two-dimensional coordinate transformations. Accordingly, the amount of required arithmetic operations can be reduced substantially as compared with the conventional method.

Although the above description was made mainly with reference to the scanning methods shown in FIGS. 2A and 2B, it is to be understood that the three-dimensional data formation method of the present invention as described above with reference to FIGS. 3 to 5 can be applied to the scanning methods shown in FIGS. 2C and 2D.

Specifically, FIG. 2C shows a case where three-dimensional data is acquired by displacing or moving the convex array transducer 10 in the direction substantially orthogonal to the scanning plane S. In this case, the scanning plane S is defined by the two-dimensional data (the depth r and the angle θ), and the amount of the displacement of the transducer 10 is defined by z. In the same manner as the case shown in FIG. 2A, the two-dimensional data (r, θ) is transformed into the two-dimensional data represented by the orthogonal two coordinates (x, Y), and thus transformed two-dimensional data (x, y) is written into an address (X, Y, Z) of the three-dimensional memory generated by the three-dimensional address generator together with the data indicating the amount z of the displacement of the scanning plane which is the relative positional information of the scanning plane.

Further, FIG. 2D shows a case where three-dimensional data is acquired by displacing or moving the linear array transducer 10 in the direction substantially orthogonal to the scanning plane S. In this case, the scanning plane S is defined by the orthogonal two-dimensional data (x', y') comprised of the value which represents the position of the ultrasound beam and the value which represents the depth of the sampling point in each ultrasound beam in the ultrasound beam direction. This orthogonal two-dimensional data (x', y') is different from the orthogonal coordinates (x, y) corresponding to the pixel arrangement. In this case, the three-dimensional data is determined by the orthogonal two-dimensional data (x', y') and the amount of the displacement of the transducer 10 defined by z. In this case, the two-dimensional data represented by (x', y') is also transformed into the two-dimensional data represented by the orthogonal two coordinates (x, Y), and thus transformed two-dimensional data (x, y) is written into an address (X, Y, Z) of the three-dimensional memory generated by the three-dimensional address generator together with the amount z of the displacement of the scanning plane which is the relative positional information of the scanning plane.

Further, although not shown in the drawing, this invention can be applied to the scanning method for pivotally rotating or swinging the linear array transducer as shown in FIG. 2D with respect to an axis which is in parallel the arrangements of the transducer elements of the linear array transducer.

Figure 6:
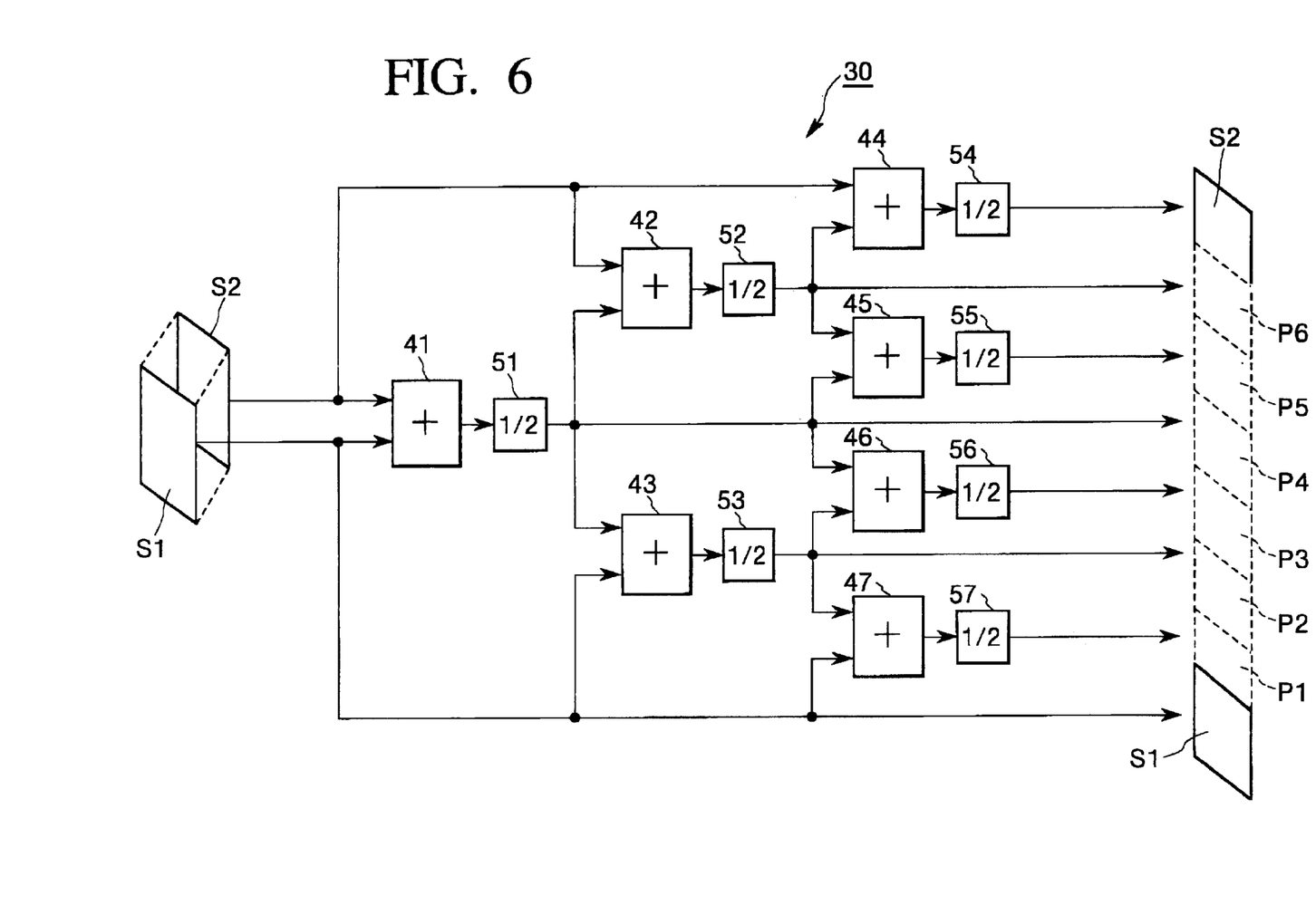
FIG. 6 is a circuit diagram which shows an example of a circuit configuration of the beam interpolation means.

FIG. 6 shows an example of configuration of the frame interpolation section 30 shown in FIG. 1. This frame interpolation section 30 is a circuit for generating six interpolated scanning planes P1 to P6 between adjacent two scanning planes S1 and S2. As shown in FIG. 6, a plurality of adders 41 to 47 are connected stepwise, and half dividers 51 to 57 are provided in each of the following stages of the respective adders 41 to 47.

By the provision of such a frame interpolation section 30, it is possible to perform interpolation processing substantially on the two-dimensional coordinate plane in the same manner as the conventional apparatus for producing the two-dimensional tomographic image. Moreover, it becomes possible to store the three-dimensional data which has been already interpolated in the three-dimensional memory 32.

As described in the above, according to the apparatus of this embodiment, the rotational axis of the scanning plane is set so as to be parallel to the x axis direction on the two-dimensional storage plane 106, and the x axis is made to coincide with the X axis in the three-dimensional storage space. Accordingly, transformation from the three-dimensional polar coordinates to the three-dimensional orthogonal coordinates can be accomplished by utilizing two times of two-dimensional coordinate transformations. With this result, it is possible to reduce the amount of arithmetic operations in comparison with the conventional apparatus, and as a result, achieve a rapid image processing. In other words, according to the three-dimensional ultrasound image processing apparatus of this embodiment, it is possible to perform the writing of three-dimensional data to the three-dimensional memory in a short time. In addition, according to this embodiment, the three-dimensional interpolation can also be performed in a short time.

Figure 7:
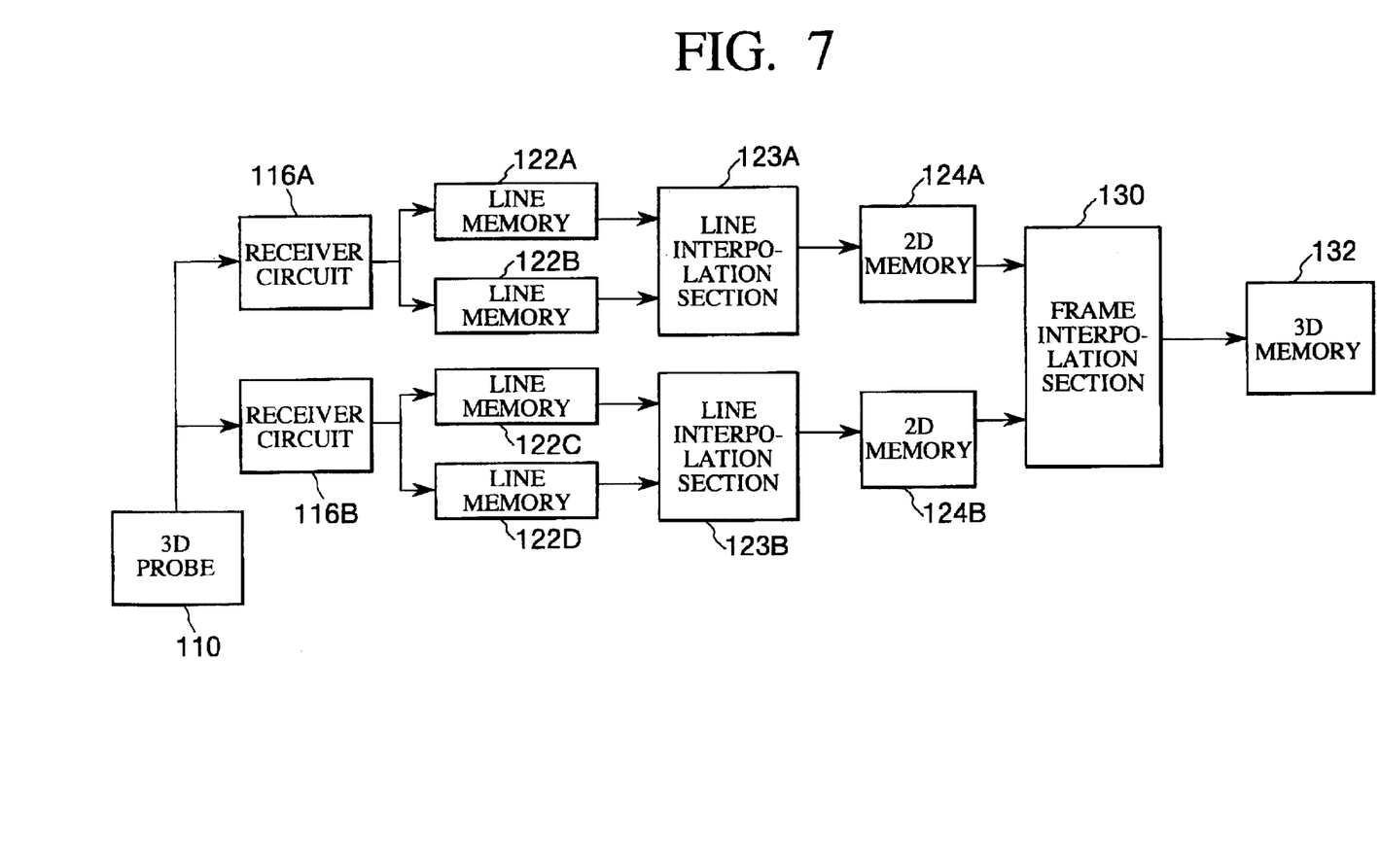
FIG. 7 is a block diagram which shows a modification of the embodiment shown in FIG. 1.

Next, FIG. 7 is a block diagram which shows a modification of the embodiment shown in FIG. 1, in which a two-dimensional array transducer provided with two-dimensionally arranged transducer elements is used in the three-dimensional probe 110. When such a two-dimensional array transducer is used in the three-dimensional probe 110, it is possible to obtain two (or more) ultrasound echoes from a three-dimensional region by one transmission of an ultrasound beam to the three-dimensional region. When the two ultrasound beams are received by the three-dimensional probe 110, the reception signals (echo signals) corresponding to the two ultrasound beams are inputted into the receiver circuits 116A, 116B, respectively.

The reception signal outputted from the receiver circuit 116A is stored in the line memories 122A, 122B in the form of two-dimensional data for one ultrasound beam, respectively. Similarly, the reception signals outputted from the receiver circuit 116B are stored in the line memories 122C, 122D in the form of two-dimensional data for one ultrasound beam, respectively. The two-dimensional data read out from the line memories 122A, 122B are inputted into the line interpolation section 123A and the two-dimensional data read out from the line memories 122C, 122D are inputted into the line interpolation section 123B, respectively, in accordance with the time sequential order. In the line interpolation sections 123A, 123B, two-dimensional interpolation data (interpolation beam) for interpolating between the adjacent beams in the scanning plane are produced.

Thus produced two-dimensional interpolation data is stored in each of the two-dimensional memories 124A, 124B with the respective scanning plane as a unit. The two-dimensional data stored in the memories 124A, 124B are data for the adjacent two scanning planes. The writing and reading out of the data in and from the two-dimensional memories 124A, 124B are controlled by a two-dimensional memory control section (not shown in the drawing).

The two-dimensional data for the two adjacent scanning planes are inputted into the frame interpolation section 130. In this frame interpolation section 130, interpolation data for one or a plurality of virtual scanning planes are produced by the interpolation calculation, thereby interpolation between the adjacent two scanning planes is performed. Then, the three-dimensional data for the three-dimensional data acquiring region are stored in the three-dimensional memory 132 in the same manner as the embodiments described with reference to the block diagram shown in FIG. 1.

In the above, a description was made with regard to the case where two receiver circuits are provided. However, the number of the receiver circuits are not limited two, and more receiver circuits may be provided taking the number of received ultrasound beams obtainable by one ultrasound beam transmission into account.

Finally, it is to be noted that the embodiments described above are only examples of the three-dimensional ultrasound image processing apparatus according to this invention, and hence it goes without saying that the scope of this invention is not limited to these embodiments. For example, this invention can be applied to sonars, radars and flaw detectors and the like. Therefore, the scope of this invention will be decided based on the accompanying claims.

What is claimed is:

1. A three-dimensional ultrasound image processing apparatus, which comprises:
   three-dimensional data acquiring means which forms scanning planes successively by ultrasound beam scanning to acquire three-dimensional data for a three-dimensional data acquiring region, each three-dimensional data being specified by two dimensional data represented by first and second values defining each scanning plane and relative positional information of the scanning plane with respect to a predetermined scanning plane;

two-dimensional coordinate transformation means for transforming the first and second values for the respective scanning plane into two-dimensional data represented by two-dimensional coordinates (x, y);

two-dimensional data storage means for sequentially storing the two-dimensional data for the respective scanning plane with one scanning plane as a unit, in which the two dimensional data for the respective scanning plane is written into an address specified by the two-dimensional coordinates (x, y) determined by the two-dimensional coordinate transformation means;

three-dimensional coordinate transformation means for transforming the three-dimensional data defined by the two-dimensional data represented by the two-dimensional coordinates (x, y) and the relative positional information of the respective scanning plane into three-dimensional data represented by three-dimensional coordinates (X, Y, Z), in which the two-dimensional coordinate x is made to correspond to the three-dimensional coordinate X;

three-dimensional data storage means for storing the three-dimensional data for each of the scanning planes which is defined by the two-dimensional data represented by the two-dimensional coordinates (x, y) outputted from the two-dimensional data storage means and the relative positional information of each scanning plane, in which the three-dimensional data for each scanning plane is written into an address specified by the three-dimensional coordinates (X, Y, Z) determined by three-dimensional coordinate transformation means; and three-dimensional ultrasound image producing means for producing a three-dimensional ultrasound image based on the three-dimensional data outputted from the three-dimensional data storage means.

2. The three-dimensional ultrasound image processing apparatus as claimed in claim 1, wherein the three-dimensional coordinate transformation means utilizes the x value of the two-dimensional coordinates as it is for the X value of the three-dimensional coordinates.

3. The three-dimensional ultrasound image processing apparatus as claimed in claim 1, wherein the two dimensional data represented by first and second values defining each scanning plane is represented by polar coordinates (r, θ).

4. The three-dimensional ultrasound image processing apparatus as claimed in claim 3, wherein the first value represents the depth r in the ultrasound beam direction, and the second value represents the angle θ of the ultrasound beam with respect to a predetermined ultrasound beam in the respective scanning plane.

5. The three-dimensional ultrasound image processing apparatus as claimed in claim 4, wherein the relative positional information of the respective scanning plane is an angle Φ of the respective scanning plane with respect to a predetermined scanning plane.

6. The three-dimensional ultrasound image processing apparatus as claimed in claim 5, wherein the predetermined scanning plane is a scanning plane initially formed.

7. The three-dimensional ultrasound image processing apparatus as claimed in claim 4, wherein the predetermined ultrasound beam in the respective scanning plane is an ultrasound beam at a scanning start position in the respective scanning plane.

8. The three-dimensional ultrasound image processing apparatus as claimed in claim 4, wherein the respective scanning plane has a center axis, and each of the three-dimensional data is written into the two-dimensional storage means so that the center axis of the respective scanning plane is in parallel with the y axis of the two-dimensional coordinates (x, y).

9. The three-dimensional ultrasound image processing apparatus as claimed in claim 8, wherein the three-dimensional data acquiring means includes an array transducer having both ends, means for causing the array transducer to perform electronic beam scanning and means for pivotally displacing the array transducer for forming the successive scanning planes with respect to a virtual rotational axis which is in parallel with a line connecting the both ends of the array transducer.

10. The three-dimensional ultrasound image processing apparatus as claimed in claim 9, wherein the displacement of the array transducer is carried out manually or by an array transducer displacement device.

11. The three-dimensional ultrasound image processing apparatus as claimed in claim 4, wherein the respective scanning plane has a center axis, and each of the three-dimensional data is written into the two-dimensional storage means so that the center axis of the respective scanning plane is in parallel with the x axis of the two-dimensional coordinates (x, y).

12. The three-dimensional ultrasound image processing apparatus as claimed in claim 11, wherein the three-dimensional data acquiring means includes an array transducer, means for causing the array transducer to perform electronic beam scanning and means for rotating the array transducer with respect to the central axis for obtaining the successive scanning planes.

13. The three-dimensional ultrasound image processing apparatus as claimed in claim 4, wherein the relative positional information of the respective scanning plane is an amount of displacement of the respective scanning plane with respect to a predetermined scanning plane.

14. The three-dimensional ultrasound image processing apparatus as claimed in claim 13, wherein the predetermined scanning plane is a scanning plane initially formed.

15. The three-dimensional ultrasound image processing apparatus as claimed in claim 13, wherein the predetermined ultrasound beam in the respective scanning plane is an ultrasound beam at a scanning start position in the respective scanning plane.

16. The three-dimensional ultrasound image processing apparatus as claimed in claim 13, wherein the three-dimensional data acquiring means includes an array transducer, means for causing the array transducer to perform electronic beam scanning and means for displacing the array transducer for forming the successive scanning planes.

17. The three-dimensional ultrasound image processing apparatus as claimed in claim 13, wherein the displacement of the scanning plane is carried out manually or by an array transducer displacement device.

18. The three-dimensional ultrasound image processing apparatus as claimed in claim 1, wherein the two dimensional data represented by first and second values defining each scanning plane is represented by orthogonal coordinates (x', y') which are different from the two-dimensional coordinates (x, y).

19. The three-dimensional ultrasound image processing apparatus as claimed in claim 18, wherein the first value represents the position of each of the ultrasound beams and the second value represents the depth of the sampling point in each ultrasound beam in the ultrasound beam direction.

20. The three-dimensional ultrasound image processing apparatus as claimed in claim 18, wherein the relative positional information of the respective scanning plane is an angle Φ of the respective scanning plane with respect to a predetermined scanning plane.

21. The three-dimensional ultrasound image processing apparatus as claimed in claim 20, wherein the predetermined scanning plane is a scanning plane initially formed.

22. The three-dimensional ultrasound image processing apparatus as claimed in claim 20, wherein the three-dimensional data acquiring means includes an array transducer having both ends, means for causing the array transducer to perform electronic beam scanning and means for pivotally displacing the array transducer for forming the successive scanning planes with respect to a virtual rotational axis which is in parallel with a line connecting the both ends of the array transducer.

23. The three-dimensional ultrasound image processing apparatus as claimed in claim 22, wherein the displacement of the array transducer is carried out manually or by an array transducer displacement device.

24. The three-dimensional ultrasound image processing apparatus as claimed in claim 18, wherein the relative positional information of the respective scanning plane is an amount of displacement of the respective scanning plane with respect to a predetermined scanning plane.

25. The three-dimensional ultrasound image processing apparatus as claimed in claim 24, wherein the predetermined scanning plane is a scanning plane initially formed.

26. The three-dimensional ultrasound image processing apparatus as claimed in claim 24, wherein the three-dimensional data acquiring means includes an array transducer, means for causing the array transducer to perform electronic beam scanning and means for displacing the array transducer for forming the successive scanning planes.

27. The three-dimensional ultrasound image processing apparatus as claimed in claim 26, wherein the displacement of the scanning plane is carried out manually or by an array transducer displacement device.

28. The three-dimensional ultrasound image processing apparatus as claimed in claim 1, further comprising interpolation means for producing interpolation data that interpolates between adjacent ultrasound beams in the respective scanning plane.

29. The three-dimensional ultrasound image processing apparatus as claimed in claim 1, further comprising scanning plane interpolation means for producing interpolation data that interpolates between adjacent scanning planes.

30. A three-dimensional ultrasound image processing apparatus, which comprises:
three-dimensional data acquiring means which forms scanning planes successively by ultrasound beam scanning to acquire three-dimensional data for a three-dimensional data acquiring region, each three-dimensional data being specified by two dimensional data defining each scanning plane and relative positional information of the scanning plane with respect to a predetermined scanning plane;
beam interpolation means for producing interpolation data that interpolates between adjacent ultrasound beams in each of the respective scanning planes, whereby forming interpolated two-dimensional data for each scanning plane;
a pair of two-dimensional data storage means for sequentially storing the interpolated two-dimensional data for the respective scanning plane with one scanning plane as a unit, respectively;
frame interpolation means for producing interpolation data that interpolates between the adjacent scanning planes using the data for the adjacent two scanning planes which are outputted from the pair of the two-dimensional data storage means and which have been undergone the beam interpolation, respectively; and
three-dimensional data storage means for storing three-dimensional data comprised of the data for the interpolated scanning planes and the relative positional information of the respective scanning; and
three-dimensional ultrasound image producing means for producing a three-dimensional ultrasound image based on the three-dimensional data outputted from the three-dimensional data storage means.

31. A coordinate transformation method used in a three-dimensional ultrasound image processing apparatus, which comprises the steps of:
forming numbers of scanning planes successively by ultrasound beam scanning to acquire three-dimensional data from a three-dimensional data acquiring region, each three-dimensional data being specified by two dimensional data represented by first and second values defining each scanning plane and relative positional information of the scanning plane with respect to a predetermined scanning plane;
transforming the first and second values for the respective scanning plane into two-dimensional data represented by two-dimensional coordinates (x, y);
sequentially storing the two-dimensional data for the respective scanning plane with one scanning plane as a unit, in which the two dimensional data for the respective scanning plane is written into an address specified by the two-dimensional coordinates (x, y) determined by the two-dimensional coordinate transformation means;
transforming the three-dimensional data defined by the two-dimensional data represented by the two-dimensional coordinates (x, y) and the relative positional information of the respective scanning plane into three-dimensional data represented by three-dimensional coordinates (X, Y, Z), in which the two-dimensional coordinate x is made to correspond to the three-dimensional coordinate X;
storing the three-dimensional data for each of the scanning planes which is defined by the two-dimensional data represented by the two-dimensional coordinates (x, y) outputted from the two-dimensional data storage means and the relative positional information of each scanning plane, in which the three-dimensional data for each scanning plane is written into an address specified by the three-dimensional coordinates (X, Y, Z) determined by three-dimensional coordinate transformation means; and
producing a three-dimensional ultrasound image based on the three-dimensional data outputted from the three-dimensional data storage means.

* * * * *